(12) United States Patent
Jiang et al.

(10) Patent No.: US 12,364,816 B2
(45) Date of Patent: Jul. 22, 2025

(54) GLUCOSE LEVEL MANAGEMENT BASED ON FAT CONTENT OF MEALS

(71) Applicant: Medtronic MiniMed, Inc., Northridge, CA (US)

(72) Inventors: Boyi Jiang, Pasadena, CA (US); Yuxiang Zhong, Arcadia, CA (US); Sinu Bessy Abraham, Gallatin, TN (US); Siddharth Arunachalam, Northridge, CA (US); Pratik J. Agrawal, Porter Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 305 days.

(21) Appl. No.: 17/180,309

(22) Filed: Feb. 19, 2021

(65) Prior Publication Data
US 2022/0265926 A1    Aug. 25, 2022

(51) Int. Cl.
*G16H 20/10*    (2018.01)
*A61M 5/172*    (2006.01)

(52) U.S. Cl.
CPC .......... *A61M 5/1723* (2013.01); *G16H 20/10* (2018.01); *A61M 2205/52* (2013.01)

(58) Field of Classification Search
CPC .................................................. G16H 20/1061
See application file for complete search history.

(56) References Cited

U.S. PATENT DOCUMENTS

| 4,562,751 A | 1/1986 | Nason et al. |
| 4,685,903 A | 8/1987 | Cable et al. |
| 5,080,653 A | 1/1992 | Voss et al. |

(Continued)

FOREIGN PATENT DOCUMENTS

| AU | 2014202301 A1 | 5/2014 |
| CN | 114949444 A | 8/2022 |

(Continued)

OTHER PUBLICATIONS

Extended Search Report from counterpart European Application No. 22156942.9 dated Jul. 7, 2022, 12 pp.

(Continued)

*Primary Examiner* — Robert A Sorey
*Assistant Examiner* — Kristine K Rapillo
(74) *Attorney, Agent, or Firm* — Weaver Austin Villeneuve & Sampson LLP

(57) ABSTRACT

Techniques for glucose level management are disclosed. In some examples, the techniques may involve obtaining an estimated protein value for a meal and determining an equivalent carbohydrate value for the meal based on the estimated protein value. In some examples, the techniques may involve obtaining an estimated fat value for a meal and determining, based on the estimated fat value, a glucose absorption rate resulting from consumption of the meal. In some examples, the equivalent carbohydrate value and/or the glucose absorption rate may be used to determine an amount of insulin to deliver to a patient to counteract a glucose level increase caused by consumption of the meal. The techniques may further involve generating an output indicative of the amount of insulin to deliver to the patient to counteract the glucose level increase caused by consumption of the meal.

20 Claims, 9 Drawing Sheets

(56) References Cited

U.S. PATENT DOCUMENTS

| | | | |
|---|---|---|---|
| 5,097,122 | A | 3/1992 | Colman et al. |
| 5,505,709 | A | 4/1996 | Funderburk et al. |
| 5,836,312 | A | 11/1998 | Moore |
| 6,088,608 | A | 7/2000 | Schulman et al. |
| 6,119,028 | A | 9/2000 | Schulman et al. |
| 6,485,465 | B2 | 11/2002 | Moberg et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,589,229 | B1 | 7/2003 | Connelly et al. |
| 6,641,533 | B2 | 11/2003 | Causey et al. |
| 6,659,980 | B2 | 12/2003 | Moberg et al. |
| 6,740,072 | B2 | 5/2004 | Starkweather et al. |
| 6,752,787 | B1 | 6/2004 | Causey, III et al. |
| 6,817,990 | B2 | 11/2004 | Yap et al. |
| 6,827,702 | B2 | 12/2004 | Lebel et al. |
| 6,932,584 | B2 | 8/2005 | Gray et al. |
| 7,323,142 | B2 | 1/2008 | Pendo et al. |
| 7,402,153 | B2 | 7/2008 | Steil et al. |
| 7,621,893 | B2 | 11/2009 | Moberg et al. |
| 8,674,288 | B2 | 3/2014 | Hanson et al. |
| 11,723,560 | B2 * | 8/2023 | Constantin ............ A61B 5/4866 705/2 |
| 2005/0187749 | A1 | 8/2005 | Singley |
| 2007/0179434 | A1 * | 8/2007 | Weinert ................. G16H 20/10 600/504 |
| 2008/0294373 | A1 | 11/2008 | Johnson |
| 2009/0006061 | A1 | 1/2009 | Thukral et al. |
| 2009/0006129 | A1 | 1/2009 | Thukral et al. |
| 2012/0315609 | A1 | 12/2012 | Miller-Kovach et al. |
| 2014/0066889 | A1 | 3/2014 | Grosman et al. |
| 2018/0169333 | A1 | 6/2018 | Grosman et al. |
| 2018/0200439 | A1 * | 7/2018 | Mazlish ............. A61M 5/1723 |
| 2018/0271455 | A1 | 9/2018 | Zhong et al. |
| 2019/0321553 | A1 | 10/2019 | Grosman et al. |
| 2019/0341137 | A1 | 11/2019 | Chiu et al. |
| 2020/0098465 | A1 | 3/2020 | Jiang et al. |
| 2020/0135320 | A1 | 4/2020 | Vleugels |
| 2020/0268968 | A1 * | 8/2020 | Steil ...................... A61M 5/172 |
| 2020/0390973 | A1 | 12/2020 | Wu et al. |
| 2021/0205534 | A1 | 7/2021 | Jepson et al. |
| 2021/0294946 | A1 * | 9/2021 | Hendriks ............... G16H 50/20 |
| 2022/0265177 | A1 | 8/2022 | Jiang et al. |

FOREIGN PATENT DOCUMENTS

| | | |
|---|---|---|
| CN | 114949445 A | 8/2022 |
| EP | 4047611 A1 | 8/2022 |
| EP | 4047612 A1 | 8/2022 |
| WO | 2019157102 A1 | 8/2019 |

OTHER PUBLICATIONS

Paterson et al., "Influence of Dietary Protein on Postprandial Blood Glucose Levels in Individuals with Type 1 Diabetes Mellitus Using Intensive Insulin Therapy," Diabetic Medicine, May 2016, vol. 33, No. 5, pp. 592-598.

Bell et al., "Impact of Fat, Protein, and Glycemic Index on Postprandial Glucose Control in Type 1 Diabetes: Implications for Intensive Diabetes Management in the Continuous Glucose Monitoring Era," Diabetes Care, vol. 38, Jun. 2015, pp. 1008-1015.

Grosman et al., "Sensor-Augmented Pump-Based Customized Mathematical Model for Type 1 Diabetes," Diabetes Technology and Therapeutics, vol. 20, No. 3, Mar. 2018, pp. 207-221.

Fletcher et al., "Feasibility of an implanted, closed-loop, blood glucose control device", Immunology 230, 2001, 31 pp., (Applicant points out, in accordance with MPEP 609.04(a), that the year of publication, 2001, is sufficiently earlier than the effective U.S. filing date, so that the particular month of publication is not an issue.).

EP Extended Search report dated Jul. 8, 2022, in U.S. Appl. No. 22/156,969.

Response to Extended Search Report dated Jul. 8, 2022, from counterpart European Application No. 22156969.2 filed Jan. 31, 2023, 18 pp.

U.S Advisory Action dated Aug. 23, 2023 in U.S. Appl. No. 17/180,268.

U.S. Final Office Action dated Jun. 2, 2023 in U.S. Appl. No. 17/180,268.

U.S. Non-Final Office Action dated Dec. 6, 2022, in U.S. Appl. No. 17/180,268.

U.S. Non-Final Office Action dated Nov. 15, 2023 in U.S. Appl. No. 17/180,268.

U.S. Advisory Action dated Aug. 30, 2024 in U.S. Appl. No. 17/180,268.

U.S. Final Office Action dated Jun. 26, 2024 in U.S. Appl. No. 17/180,268.

* cited by examiner

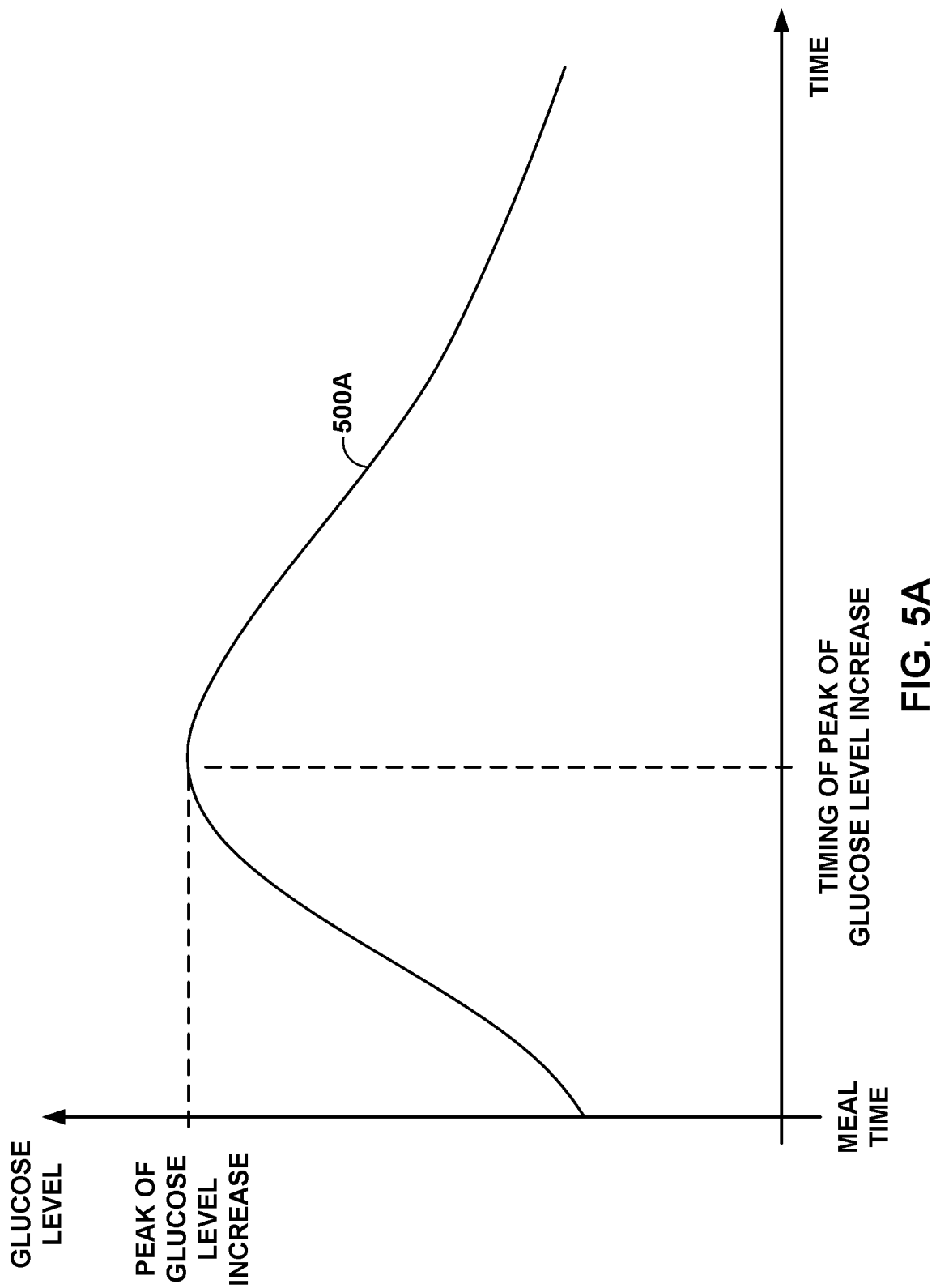

GLUCOSE LEVEL MANAGEMENT BASED ON FAT CONTENT OF MEALS

TECHNICAL FIELD

The disclosure relates to medical systems and, more particularly, to medical systems for therapy for diabetes.

BACKGROUND

A patient with diabetes typically receives insulin from an insulin delivery device (e.g., a pump or injection device) to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include basal dosages and bolus dosages of insulin. Basal dosages tend to keep glucose levels at consistent levels during periods of fasting. Bolus dosages may be delivered to the patient specifically at or near mealtimes or other times where there may be a relatively fast change in glucose level.

SUMMARY

Disclosed herein are techniques for glucose level management. The techniques may be practiced using systems; processor-implemented methods; and non-transitory processor-readable storage media storing instructions which, when executed by one or more processors, cause performance of the techniques.

In some embodiments, the techniques may involve obtaining a fat value for a meal. The techniques may further involve determining, based on the estimated fat value, a glucose absorption rate resulting from consumption of the meal. The techniques may also involve determining, based on the glucose absorption rate resulting from consumption of the meal, an amount of insulin to deliver to a patient to counteract a glucose level increase caused by consumption of the meal. Additionally, the techniques may involve generating an output indicative of the amount of insulin to deliver to the patient to counteract the glucose level increase caused by consumption of the meal.

The details of one or more aspects of the disclosure are set forth in the accompanying drawings and the description below. Other features, objects, and advantages of this disclosure will be apparent from the description and drawings, and from the claims.

BRIEF DESCRIPTION OF DRAWINGS

FIGS. 5A and 5B are example plots of glucose level over time after consuming a meal.

DETAILED DESCRIPTION

Figure 1:
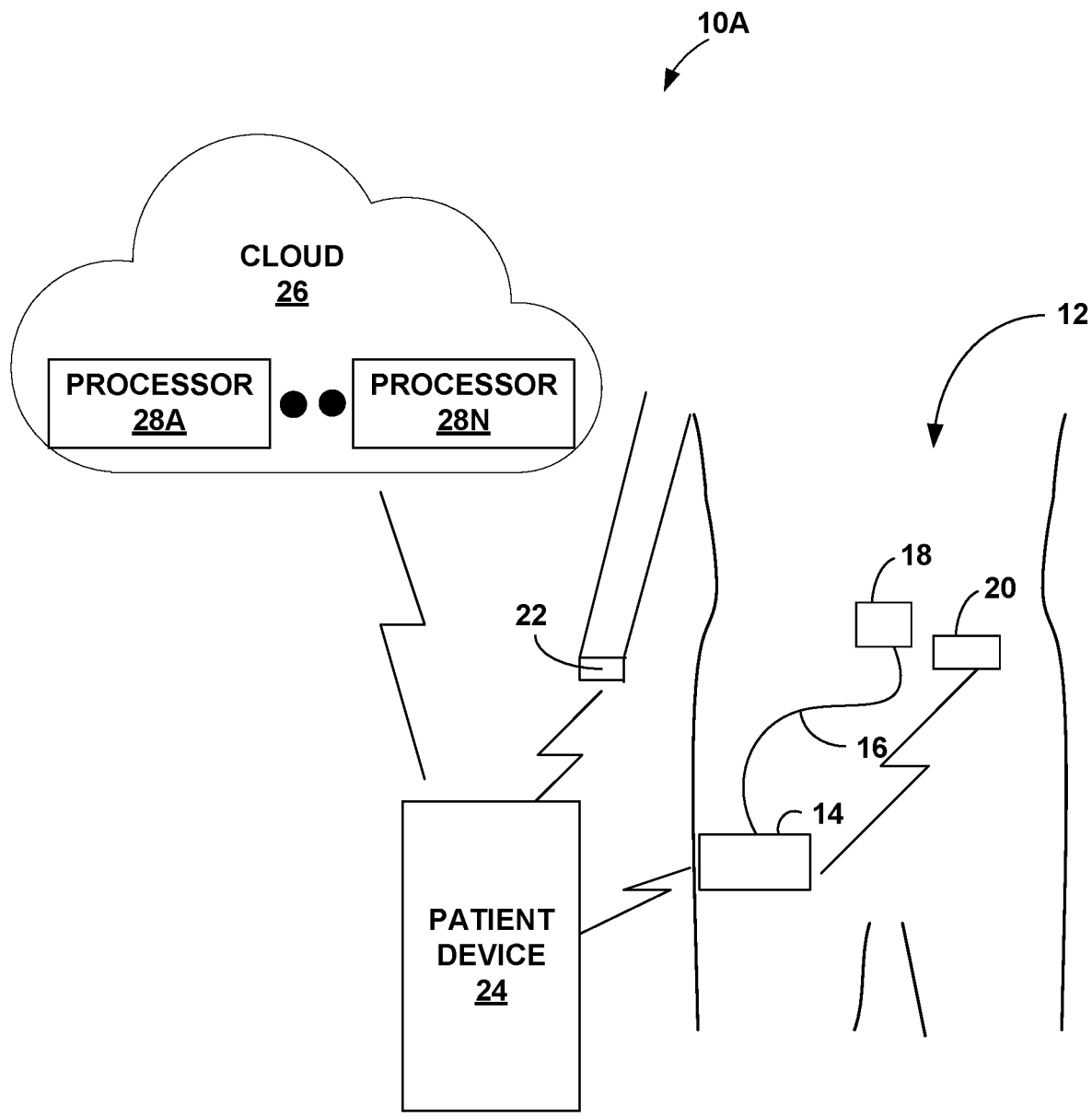
FIG. 1 is a block diagram illustrating an example glucose level management system comprising an insulin pump, in accordance with one or more examples described in this disclosure.

Disclosed herein are devices, systems, and techniques for managing a glucose level of a patient based on information about one or more macronutrients (e.g., protein and/or fat) other than carbohydrates. A patient's glucose level after consuming a meal is heavily influenced by the carbohydrate content of the meal. In general, for meals with higher carbohydrate contents, higher glucose levels are expected for the patient after consuming the meal. However, managing glucose levels based only on the carbohydrate content of the meal fails to account for other macronutrients that impact glucose levels. For example, the protein content and/or the fat content of the meal can affect the glucose level of the patient after consuming the meal.

To account for other macronutrients in the meal, a physiological model of the patient may be configured to take, as input, information about one or more macronutrients other than carbohydrates. For example, a computing device of this disclosure may be configured to create an equivalent carbohydrate content for the meal based on the protein content of the meal. One gram of protein may not have the same effect on glucose levels as one gram of carbohydrates, so the computing device may use a conversion factor to scale a value of the protein content. Additionally or alternatively, the fat content of the meal may affect the rate at which the patient's body absorbs glucose after consuming the meal. Thus, meals differing in fat content may have different peak glucose levels after the meal and/or different timings of the peak glucose levels after the meal. Accordingly, the computing device may use a tuning factor to approximate the effect of the fat content on glucose levels. More specifically, the tuning factor may be used to approximately the effect of the fat content on reducing the rate at which the patient's body absorbs glucose. In some examples, a tuning factor with a large magnitude limits the effect of fat on reducing the absorption rate more so than a tuning factor with a small magnitude. In graphical terms, the glucose profile (e.g., plot of glucose levels over time) corresponding to a fatty meal may appear to be a flattened curve (e.g., having a peak glucose level that is lower and that occurs later in time) relative to a glucose profile corresponding to a meal without fat.

By accounting for the protein content and/or the fat content of a meal, a computing device implementing the physiological model may predict postprandial glucose levels with greater accuracy. Additionally or alternatively, the computing device may determine a meal bolus dosage that will maximize time-in-range.

It should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

FIG. 1 is a block diagram illustrating an example glucose level management system, in accordance with one or more examples described in this disclosure. FIG. 1 illustrates system 10A that includes insulin pump 14, tubing 16, infusion set 18, monitoring device 20 (e.g., a glucose level monitoring device), wearable device 22, patient device 24, and cloud 26. Cloud 26 represents a local, wide area or global computing network including one or more processors 28A-28N ("one or more processors 28"). In some examples, the various components may determine changes to therapy based on determination of glucose level for monitoring device 20, and therefore system 10A may be referred to as glucose level management system 10A.

Patient 12 may be diabetic (e.g., Type 1 diabetic or Type 2 diabetic), and therefore, the glucose level in patient 12 may be controlled with delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Monitoring device 20 may also be coupled to patient 12 to measure glucose level in patient 12. Insulin pump 14, tubing 16, infusion set 18, and monitoring device 20 may together form an insulin pump system. One example of the insulin pump system is the MINIMED™ 670G insulin pump system by MEDTRONIC MINIMED, INC. However, other examples of insulin pump systems may be used and the example techniques should not be considered limited to the MINIMED™ 670G insulin pump system. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or monitoring device 20 may be contained in the same housing.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places, and patient 12 may place insulin pump 14 in a location based on the particular clothes patient 12 is wearing. Other insulin delivery devices (e.g., injection devices, inhaler devices, etc.) may be used in addition to or as an alternative to insulin pump 14.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery-powered device that is powered by replaceable and/or rechargeable batteries.

Tubing 16 may connect at a first end to a reservoir in insulin pump 14 and may connect at a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin may travel from the reservoir of insulin pump 14, through tubing 16, through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Monitoring device 20 may include a sensor that is inserted under the skin of patient 12, such as near the stomach of patient 12 or in the arm of patient 12 (e.g., subcutaneous connection). Monitoring device 20 may be configured to measure the interstitial glucose level, which is the glucose found in the fluid between the cells of patient 12. Monitoring device 20 may be configured to continuously or periodically sample the glucose level and rate of change of the glucose level over time.

In one or more examples, insulin pump 14, monitoring device 20, and/or the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from monitoring device 20 and, in response, may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

Insulin pump 14 and monitoring device 20 may be configured to operate together to mimic some of the ways in which a healthy pancreas works. Insulin pump 14 may be configured to deliver basal dosages, which are small amounts of insulin released continuously throughout the day. There may be times when glucose levels increase, such as due to eating or some other activity that patient 12 undertakes. Insulin pump 14 may be configured to deliver bolus dosages on demand in association with food intake or to correct an undesirably high glucose level in the bloodstream. In one or more examples, if the glucose level rises above a target level, then insulin pump 14 may deliver a bolus dosage to address the increase in glucose level. Insulin pump 14 may be configured to compute basal and bolus dosages and deliver the basal and bolus dosages accordingly. For instance, insulin pump 14 may determine the amount of a basal dosage to deliver continuously and then determine the amount of a bolus dosage to deliver to reduce glucose level in response to an increase in glucose level due to eating or some other event.

Accordingly, in some examples, monitoring device 20 may sample glucose levels for determining rate of change in glucose level over time. Monitoring device 20 may output the glucose level to insulin pump 14 (e.g., through a wireless link connection like Bluetooth or BLE). Insulin pump 14 may compare the glucose level to a target glucose level (e.g., as set by patient 12 or a clinician) and adjust the insulin dosage based on the comparison.

As described above, patient 12 or a clinician may set one or more target glucose levels on insulin pump 14. There may be various ways in which patient 12 or the clinician may set a target glucose level on insulin pump 14. As one example, patient 12 or the clinician may utilize patient device 24 to communicate with insulin pump 14. Examples of patient device 24 include mobile devices, such as smartphones, tablet computers, laptop computers, and the like. In some examples, patient device 24 may be a special programmer or controller (e.g., a dedicated remote control device) for insulin pump 14. Although FIG. 1 illustrates one patient device 24, in some examples, there may be a plurality of patient devices. For instance, system 10A may include a mobile device and a dedicated wireless controller, each of which is an example of patient device 24. For ease of description only, the example techniques are described with respect to patient device 24 with the understanding that patient device 24 may be one or more patient devices.

Patient device 24 may also be configured to interface with monitoring device 20. As one example, patient device 24 may receive information from monitoring device 20 through insulin pump 14, where insulin pump 14 relays the information between patient device 24 and monitoring device 20. As another example, patient device 24 may receive information (e.g., glucose level or rate of change of glucose level) directly from monitoring device 20 (e.g., through a wireless link). Patient device 24 may include processing circuitry configured to receive user input indicative of macronutrient values for a meal that patient 12 has consumed, is consuming, or will consume.

In one or more examples, patient device 24 may comprise a user interface with which patient 12 or the clinician may control insulin pump 14. For example, patient device 24 may comprise a touchscreen that allows patient 12 or the clinician to enter a target glucose level. Additionally or alternatively, patient device 24 may comprise a display device that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through a display device of patient device 24 is merely provided as an example and should not be considered limiting. For example, insulin pump 14 may include pushbuttons that allow patient 12 or the clinician to set the various glucose levels of insulin pump 14. In some examples, insulin pump 14 itself, or in addition to patient device 24, may be configured to output notifications to patient 12. For instance, if the glucose level is too high or too low, insulin pump 14 may output an audible or haptic output. In some examples, if the battery is low, then insulin pump 14 may output a low battery indication on a display of insulin pump 14.

As mentioned above, insulin pump 14 may deliver insulin to patient 12 based on current glucose levels (e.g., as measured by monitoring device 20). However, it should be appreciated that insulin delivery is not limited to implementations based on current glucose levels. For example, insulin pump 14 may deliver insulin to patient 12 based on a predicted glucose level (e.g., a future glucose level that is determined based on a glucose level trend).

The glucose level of patient 12 may be affected by patient 12 engaging in an activity like eating or exercising. There may be therapeutic benefits to delivering/not delivering insulin based on determining that patient 12 is engaging in the activity.

As illustrated in FIG. 1, patient 12 may wear wearable device 22. Examples of wearable device 22 include a smartwatch or a fitness tracker, either of which may, in some examples, be configured to be worn on a patient's wrist or arm. In one or more examples, wearable device 22 includes an inertial measurement unit, such as a six-axis inertial measurement unit. The inertial measurement unit may include an accelerometer (e.g., a 3-axis accelerometer) and a gyroscope (e.g., a 3-axis gyroscope). Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. For example, patient 12 may wear wearable device 22 on a finger, forearm, or bicep. In general, patient 12 may wear wearable device 22 anywhere that can be used to determine gestures indicative of eating.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency with which patient 12 moves his or her arm or a pattern with which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect any activity undertaken by patient 12. For instance, the movement characteristics detected by wearable device 22 may indicate whether patient 12 is exercising, driving, sleeping, etc. In some examples, wearable device 22 may detect a posture of patient 12 that corresponds with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to one or more other devices (e.g., patient device 24 and/or one or more server computers in cloud 26), and the one or more other devices may be configured to determine the activity patient 12 is undertaking.

As illustrated in FIG. 1, system 10A includes cloud 26 that includes one or more processors 28. For example, cloud 26 may include a plurality of network devices (e.g., servers), and each network device may include one or more processors. One or more processors 28 may be distributed across the plurality of network devices or may be located within a single one of the network devices. Cloud 26 represents a computing infrastructure that supports one or more processors 28 which may execute applications or operations requested by one or more users. For example, one or more processors 28 may remotely store, manage, and/or process data that would otherwise be locally stored, managed, and/or processed by patient device 24 or wearable device 22. One or more processors 28 may share data or resources for performing computations and may be part of computing servers, web servers, database servers, and the like. One or more processors 28 may be in network devices (e.g., servers) within a datacenter or may be distributed across multiple datacenters. In some cases, the datacenters may be in different geographical locations.

One or more processors 28, as well as other processing circuitry described herein, can include one or more of any of the following: microprocessors, digital signal processors (DSPs), application specific integrated circuits (ASICs), field programmable gate arrays (FPGAs), or any other equivalent integrated or discrete logic circuitry, as well as any combinations of such components. The functions attributed to one or more processors 28, as well as other processing circuitry described herein may be embodied as hardware, firmware, software, or any combination thereof.

One or more processors 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more processors 28 may include distinct circuit blocks (fixed-function or programmable), and in some examples, one or more processors 28 may include integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on servers in cloud 26) accessible by one or more processors 28 may store the object code of the software that one or more processors 28 receive and execute.

In some examples, one or more processors 28 may be configured to determine patterns from gesture movements (e.g., one or more movement characteristics determined by wearable device 22) and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). Cloud 26 and patient device 24 may communicate via one or more networks (e.g., a wired network, a wireless network, and/or a carrier network).

For example, as described above, in some examples, wearable device 22 and/or patient device 24 may be configured to determine that patient 12 is undertaking an activity. However, in some examples, patient device 24 may output information indicative of the movement characteristics of movement of the arm of patient 12 to cloud 26 with contextual information like location or time of day. One or more processors 28 of cloud 26 may then determine the activity patient 12 is undertaking. Insulin pump 14 may then deliver insulin based on the determined activity of patient 12.

One example way in which one or more processors 28 may be configured to determine that patient 12 is undertaking an activity and determine therapy to deliver is described in U.S. Patent Publication No. 2020/0135320 A1, the entirety of which is incorporated by reference herein.

The above describes arm movement as a factor in determining whether patient 12 is engaging in an activity. However, there may be various other factors that can be used separately or in combination with arm movement to determine whether patient 12 is engaging in an activity. Time of day and location are two examples of contextual information that can be used to determine whether patient 12 is engaging in the activity. For instance, patient 12 may engage in the activity at regular time intervals and/or at certain locations. Such other factors may be communicated to one or more processors 28 in any of a variety of ways. For example, patient device 24 may output information about the time of day and the location of patient 12. In some embodiments, patient device 24 may be equipped with a positioning device, such as a global positioning system (GPS) unit, and patient device 24 may output location information determined by the GPS unit. In some embodiments, location information may be determined based on known locations of wireless access points and/or cell towers.

There may be various other ways in which one or more processors 28 may determine the activity patient 12 is undertaking. This disclosure provides some example techniques for determining the activity patient 12 is undertaking, but the example techniques should not be considered limiting.

In some examples, one or more processors 28 may be configured to determine an amount of insulin (e.g., a bolus dosage of insulin) to deliver to patient 12. As one example, memory accessible by one or more processors 28 may store patient-specific parameters of patient 12 (e.g., an insulin sensitivity factor, an insulin-to-carbohydrate ratio, etc.). One or more processors 28 may access the memory and, based on the type of food patient 12 is eating and the patient-specific parameters, may determine the amount of insulin that patient 12 is to receive.

In some examples, the amount of insulin may be determined based on a patient-specific physiological simulator referred to herein as a "digital twin." One or more processors 28 may be configured to utilize a "digital twin" of patient 12 to determine, in a manner that accounts for various idiosyncrasies of patient 12, an amount of insulin to be delivered to patient 12. A digital twin may be a digital replica of patient 12 that is based on a mathematical model having one or more patient-specific parameters (e.g., insulin sensitivity factor, body weight, endogenous glucose production, speed of carbohydrate absorption, and/or speed of insulin absorption). The digital twin may be implemented via software executing on one or more processors 28. The digital twin may take, as input, information about what patient 12 ate and use this information to simulate postprandial glucose levels and/or to generate a recommendation of how much insulin to deliver to patient 12 to control the increase in glucose level resulting from meal consumption.

For example, information about the macronutrient content (e.g., carbohydrates, protein, and/or fat content) of a meal may be provided to a digital twin of patient 12. Based on the macronutrient content, the digital twin may be used to predict a time series of glucose amounts to be absorbed into the bloodstream of patient 12. This may involve converting an estimated amount of protein into a corresponding amount of carbohydrates. Additionally or alternatively, this may involve determining the impact of an estimated amount of fat on the rate of glucose absorption by the digestive system into the bloodstream.

The predicted time series of glucose amounts may be used for a variety of different purposes (e.g., generating an insulin dosage recommendation). In some embodiments, the predicted time series of to-be-absorbed glucose amounts may be used in conjunction with an amount of insulin (e.g., a basal dosage and/or a bolus dosage) to predict a time series of glucose levels (e.g., blood glucose levels or interstitial glucose levels) resulting from consumption of the meal and delivery of the amount of insulin. In some embodiments, the predicted time series of resulting glucose levels may be used to determine an amount of insulin that is "optimal" in that the amount of insulin maximizes time-in-range. For instance, the digital twin may predict a respective time series of resulting glucose levels for each candidate dosage of a plurality of candidate dosages, and each time series of resulting glucose levels may be evaluated to determine how many of the resulting glucose levels fall within a target range (e.g., a predetermined target range having an upper limit that is a predetermined number of values below a hyperglycemic glucose level and a lower limit that is a predetermined number of values above a hypoglycemic glucose level). The candidate dosage that is selected for recommendation may correspond to the time series of resulting glucose levels exhibiting a maximum amount of time (e.g., relative to other time series of resulting glucose levels) within the target range.

One or more processors 28 may communicate the recommendation to patient device 24. Responsive to obtaining the recommendation, patient device 24 may cause insulin pump 14 to deliver the recommended amount of insulin. For example, patient device 24 may communicate to insulin pump 14 the amount of insulin to deliver.

As described above, a prediction model, such as the digital twin, may utilize information indicative of the carbohydrates, protein, and/or fat content of a meal to determine an amount of insulin sufficient to counteract a change in glucose level due to consumption of the meal. Using protein and/or fat, in addition to carbohydrates, to determine an insulin dosage may result in a more accurate dosage determination as compared to examples where only carbohydrates are utilized. This is because protein and fat can affect the amount and/or timing of a meal bolus that is sufficient to counteract a glucose level increase caused by meal consumption.

Figure 2:
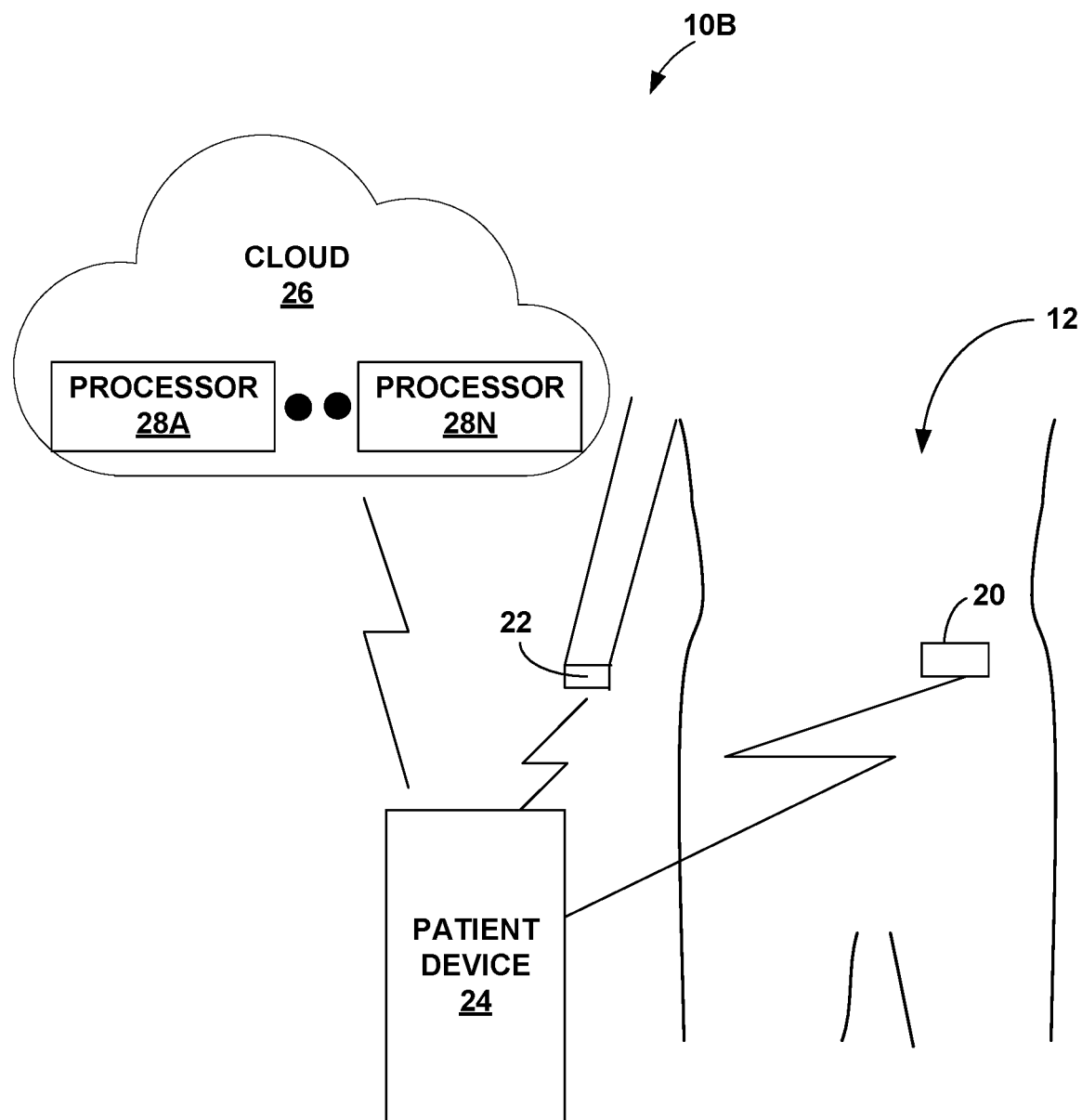
FIG. 2 is a block diagram illustrating an example glucose level management system comprising a manual injection device, in accordance with one or more examples described in this disclosure.

FIG. 2 is a block diagram illustrating an example glucose level management system comprising a manual injection device (not shown), in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or a caretaker of patient 12) may fill a syringe with insulin, set the dosage amount in an insulin pen, and/or perform an injection. One or more processors 28 may use the techniques of this disclosure to generate an output indicative of an amount of insulin to deliver to patient 12. One or more processors 28 may communicate the output to patient device 24 to present the output via a user interface of patient device 24. Patient 12 (or a caretaker) may use the output to provide therapy accordingly.

Figure 3:
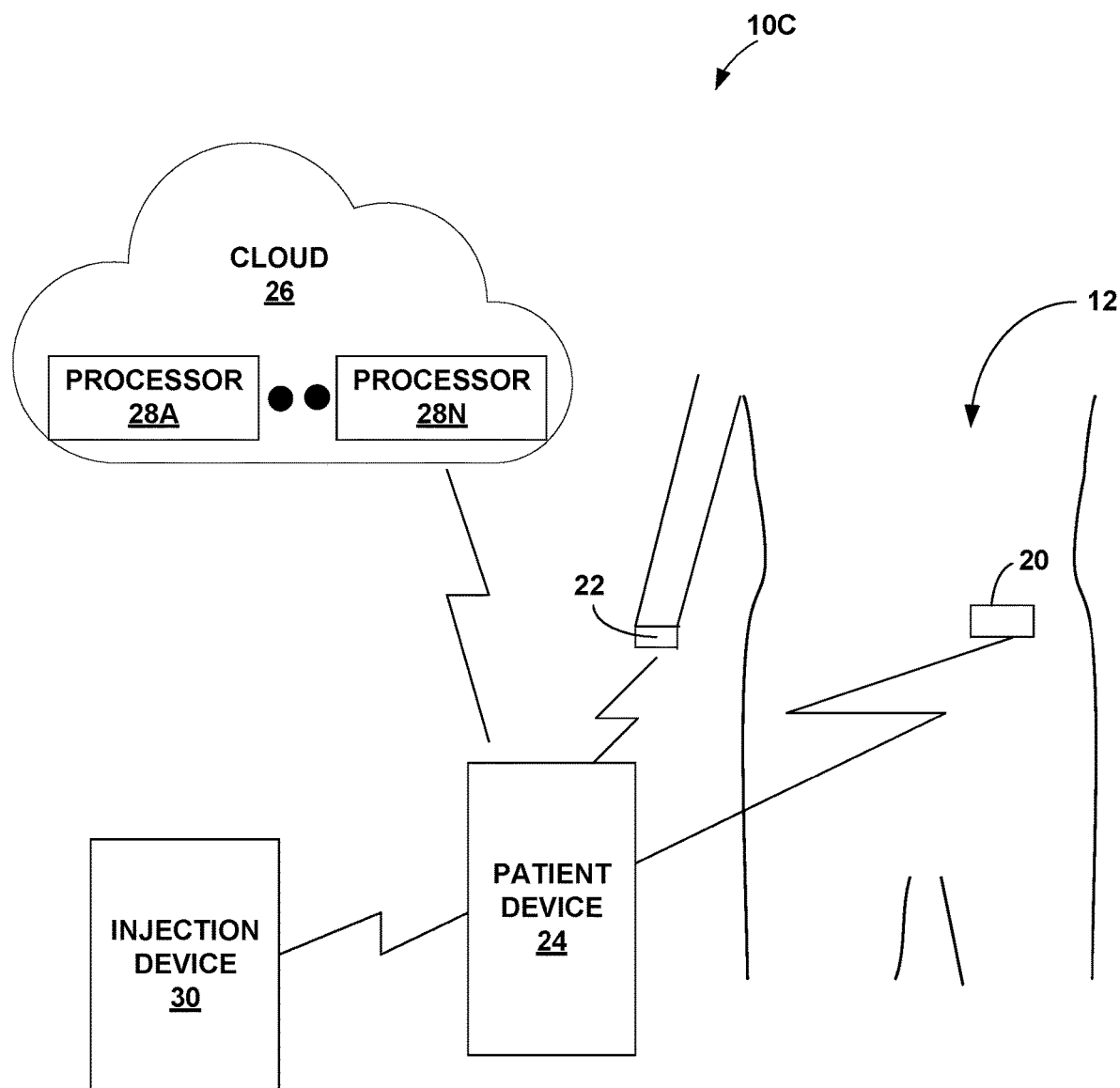
FIG. 3 is a block diagram illustrating an example glucose level management system comprising a networked injection device, in accordance with one or more examples described in this disclosure.

FIG. 3 is a block diagram illustrating an example glucose level management system comprising a networked injection device, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or a caretaker of patient 12) may utilize injection device 30 to perform an injection.

Injection device 30 may be different than a syringe because injection device 30 may be a device that can communicate with patient device 24 and/or other devices in system 10C. Also, injection device 30 may include a reservoir and, based on information indicative of how much therapy dosage to deliver, may be able to dose out that much insulin for delivery. For example, injection device 30 may automatically set the amount of insulin based on the information received from patient device 24. In some examples, injection device 30 may be similar to insulin pump 14 but not worn by patient 12. One example of injection device 30 is an insulin pen, sometimes also called a smart insulin pen. Another example of injection device 30 may be an insulin pen with a smart cap, where the smart cap can be used to set particular doses of insulin. One or more processors 28 may use the techniques of this disclosure to generate an output indicative of an amount of insulin to deliver to patient 12. One or more processors 28 may be configured to communicate the output to patient device 24 and/or injection device 30 to automatically set the determined amount of insulin to be delivered to patient 12.

The above examples describe insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be a powered (e.g., battery-powered) device, and the syringe may be a device that requires no power.

Figure 4:
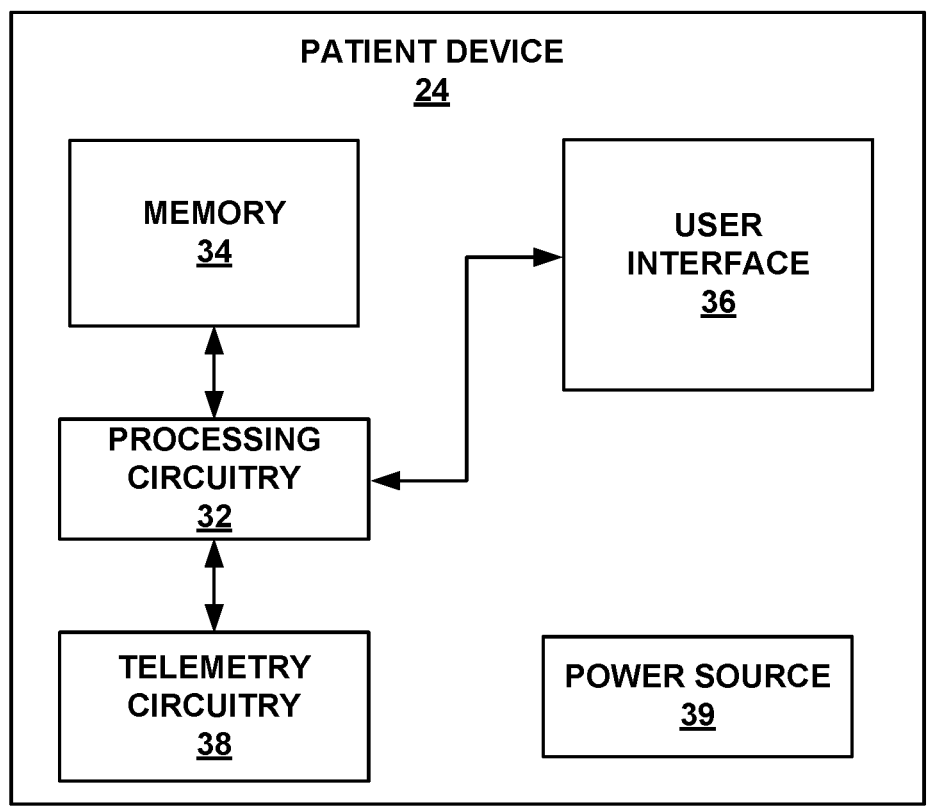
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, in some embodiments, patient device 24 may be a notebook computer or a workstation, for example. In some examples, patient device 24 may be a mobile device, such as a smartphone or a tablet computer. Patient device 24 may execute an application that allows patient device 24 to perform example techniques described in this disclosure. For example, processing circuitry 32 of patient device 24 may be configured to obtain user input indicative of one or more macronutrient values for a meal, communicate the one or more macronutrient values to one or more processors 28, and obtain a dosage recommendation indicative of an amount of insulin sufficient to counteract a glucose level increase caused by consumption of the meal. In some examples, patient device 24 may be a specialized controller for communicating with insulin pump 14.

As illustrated in FIG. 4, patient device 24 may include processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure. For example, processing circuitry 32 may be configured to obtain user input indicative of one or more macronutrient values for a meal.

In some examples, memory 34 of patient device 24 may store a plurality of parameters, such as amounts of insulin to deliver, target glucose level, time of delivery, etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification to take insulin, amount of insulin, and time to take the insulin, via user interface 36.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a microphone for voice commands, and/or a display, such as a liquid crystal display (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of the macronutrient content of a meal, whether patient 12 took the insulin (e.g., through the syringe or injection device 30), and other such information.

Telemetry circuitry 38 includes any suitable hardware, firmware, software, or any combination thereof for communicating with another device, such as a device in cloud 26, insulin pump 14 or injection device 30, as applicable, wearable device 22, and monitoring device 20. Telemetry circuitry 38 may receive communication with the aid of an antenna, which may be internal and/or external to patient device 24. Telemetry circuitry 38 may be configured to communicate with another computing device via wireless communication techniques or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may last for several months or years, while a rechargeable battery may be periodically charged from an external device, e.g., on a daily or weekly basis. Recharging of a rechargeable battery may be accomplished by using an alternating current (AC) outlet or through proximal inductive interaction between an external charger and an inductive charging coil within patient device 24.

FIG. 5A is an example glucose profile 500A comprising a plot of glucose level over time after consuming a meal. The plot shown in FIG. 5A depicts the time at which the meal is consumed as time zero. In some examples, one or more processors 28 may simulate glucose level over time under the assumption that the meal is consumed instantaneously. In other words, one or more processors 28 may model the meal as a set of macronutrient values consumed by patient 12 at a single point in time. Alternatively, one or more processors 28 may be configured to model the meal as a set of macronutrient values consumed by patient 12 over a non-instantaneous period of time. For example, one or more processors 28 can model the meal as a set of two or more impulses over a period of time, as one or more rectangular waveforms, as one or more triangular waveforms, as one or more trapezoidal waveforms, and/or any combination thereof.

When patient 12 consumes the meal, patient 12's glucose level increases to a peak of the glucose level increase at a time labeled "timing of the peak of the glucose level increase." After reaching the peak of the glucose level increase (e.g., the maximum glucose level), patient 12's glucose level decreases. Glucose profile 500A may represent blood glucose levels as a function of time. Glucose profile 500A may be affected by the net movement of glucose molecules into and out of the bloodstream. Glucose molecules entering the bloodstream from the digestive system may contribute to a glucose level increase, and glucose molecules exiting the bloodstream due to the effects of insulin may contribute to a glucose level decrease. Preferably, the insulin is delivered to patient 12 in an amount that is sufficient to keep the peak of the glucose level increase below an upper limit of a target range as well as to keep subsequent glucose levels above a lower limit of the target range.

Among the factors affecting glucose profile 500A is the glucose absorption rate of the digestive system. As the consumed meal passes through the digestive system of patient 12, the digestive system absorbs some of the molecules of the meal. In some examples, the rate of absorption of molecules (e.g., glucose molecules) may be based on the quantity of molecules that are passing through the digestive system (e.g., the stomach and intestines). In general, the larger the number of glucose molecules in the digestive system, the higher the rate of absorption of glucose molecules from the digestive system into the bloodstream. The number of glucose molecules in the digestive system may be determined by the net movement of glucose molecules into and out of the digestive system. As the digestive system absorbs glucose molecules into the bloodstream of patient 12, the number of glucose molecules in the digestive system may decrease. However, as glucose molecules are introduced into the digestive system by the meal, the number of glucose molecules in the digestive system may increase.

Figure 5B:
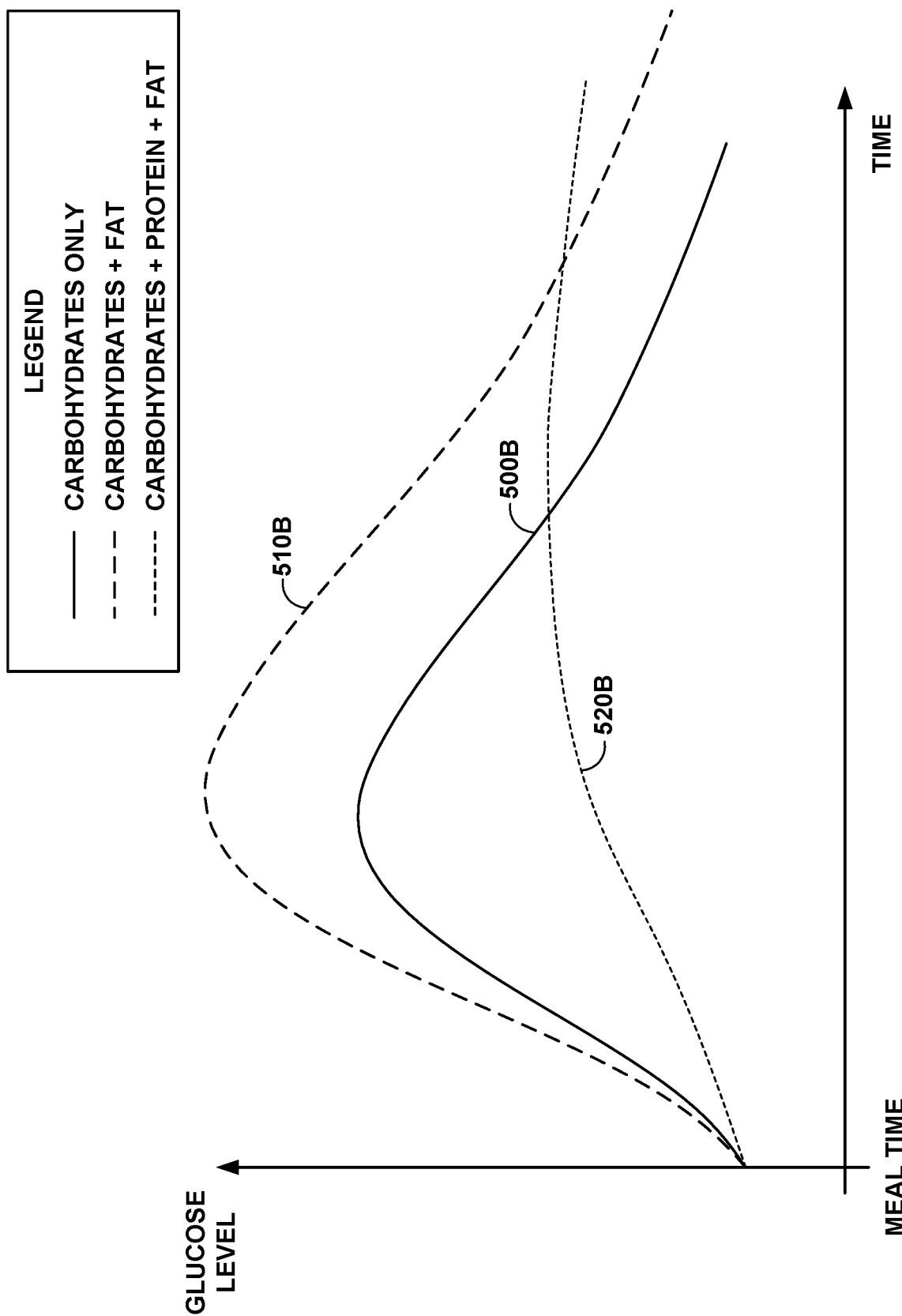

FIG. 5B is an example plot of glucose profiles 500B, 510B, and 520B over time after consuming a meal. As mentioned above, a meal can include a number of macronutrients (e.g., carbohydrates, protein, and/or fat), each of which can affect the glucose absorption rate of the digestive system. Thus, using a simplistic prediction model that accounts for only the carbohydrate content of a meal may result in glucose level mismanagement. For example, ten grams of protein may have the same effect on glucose levels as one gram of carbohydrates. Thus, failing to account for the protein content of a meal may result in underestimating the glucose level increase caused by the meal and/or underestimating the amount of insulin for counteracting the glucose level increase. Glucose profile 500B represents the glucose level over time after consuming a meal including only carbohydrates (i.e., a control group). Glucose profile 510B represents the glucose level over time after consuming a meal including carbohydrates and protein. The peak of glucose profile 510B is higher than the peak of glucose profile 500B because the protein in the meal represented by glucose profile 510B is equivalent to an amount of carbohydrates.

As another example, fat can affect the timing and magnitude of the peak of the glucose level increase, because fat may cause a decrease in the glucose absorption rate of the digestive system. More specifically, the fat content of a meal may delay the timing of the peak of the glucose level increase and reduce the magnitude of the peak of the glucose level increase. Moreover, the fat content of a meal may cause glucose levels to remain elevated at or near the peak of the glucose level increase for a prolonged period of time. Thus, prematurely determining the peak of the glucose level increase and assuming that the peak of the glucose level increase is short-lived can result in determining an insulin dosage that is insufficient to counteract the glucose level increased caused by the meal. Glucose profile 520B represents the glucose level over time after consuming a meal including carbohydrates, fat, and protein. The peak of glucose profile 520B is lower and delayed as compared to the peak of glucose profile 500B because the meal represented by glucose profile 520B has a fat content that slows the absorption of carbohydrates. For a meal with a relatively low fat content, the peak of the glucose level increase may have a magnitude that is closer to the peak of the glucose level caused by a carbohydrate-only meal.

Figure 6:
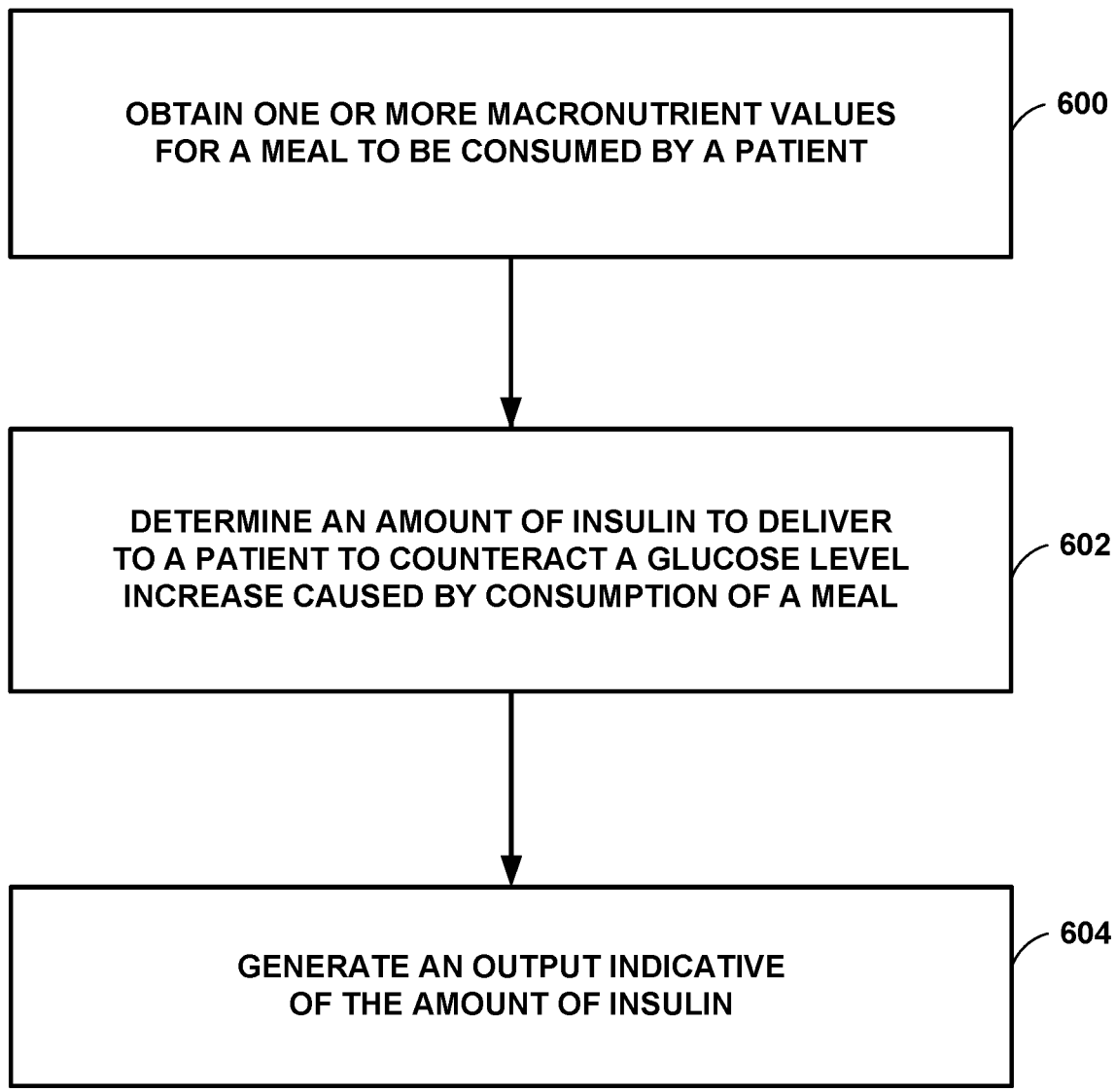
FIGS. 6-8 are flow diagrams illustrating example techniques for glucose level management, in accordance with the techniques of this disclosure.
Figure 7:
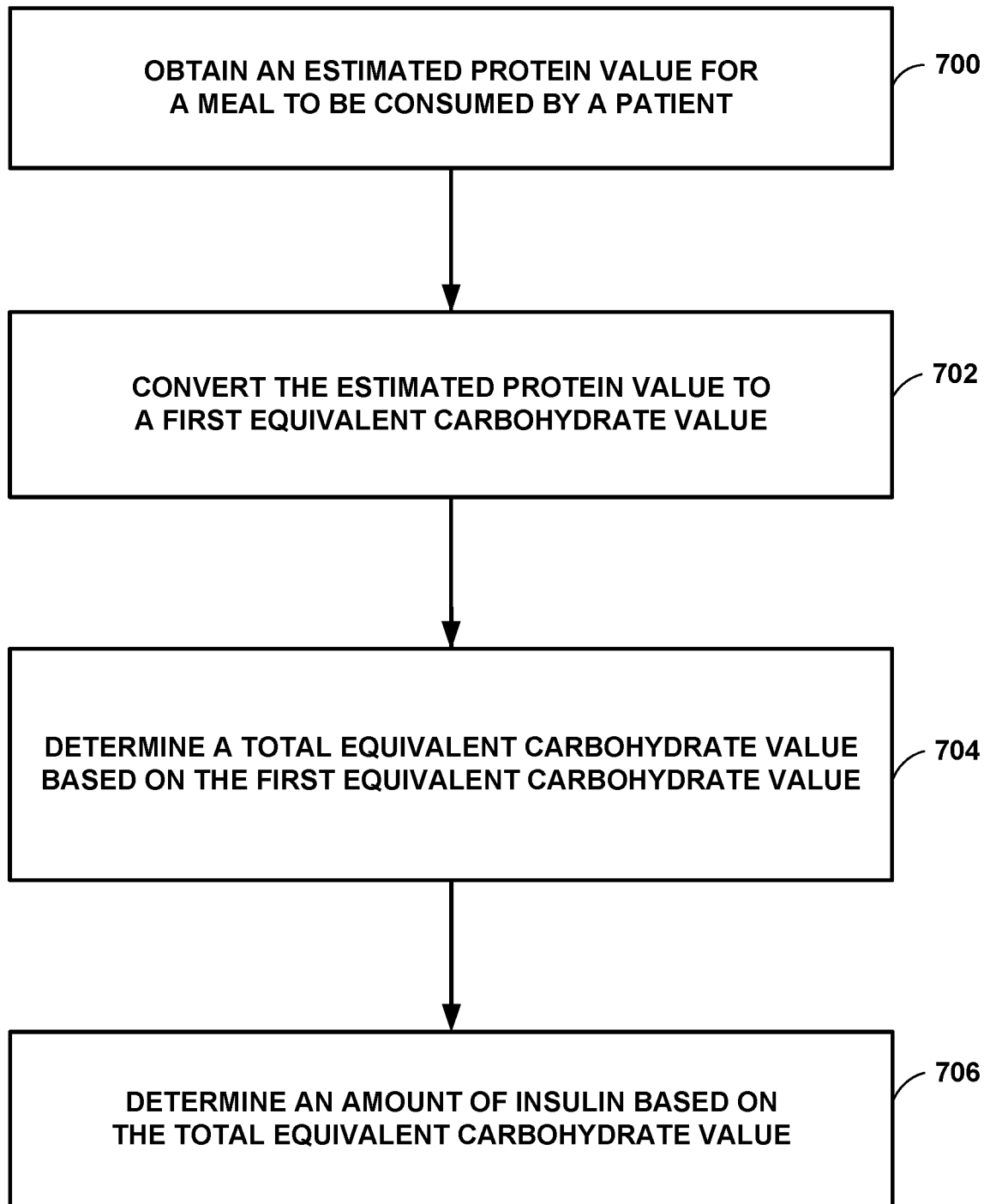
Figure 8:
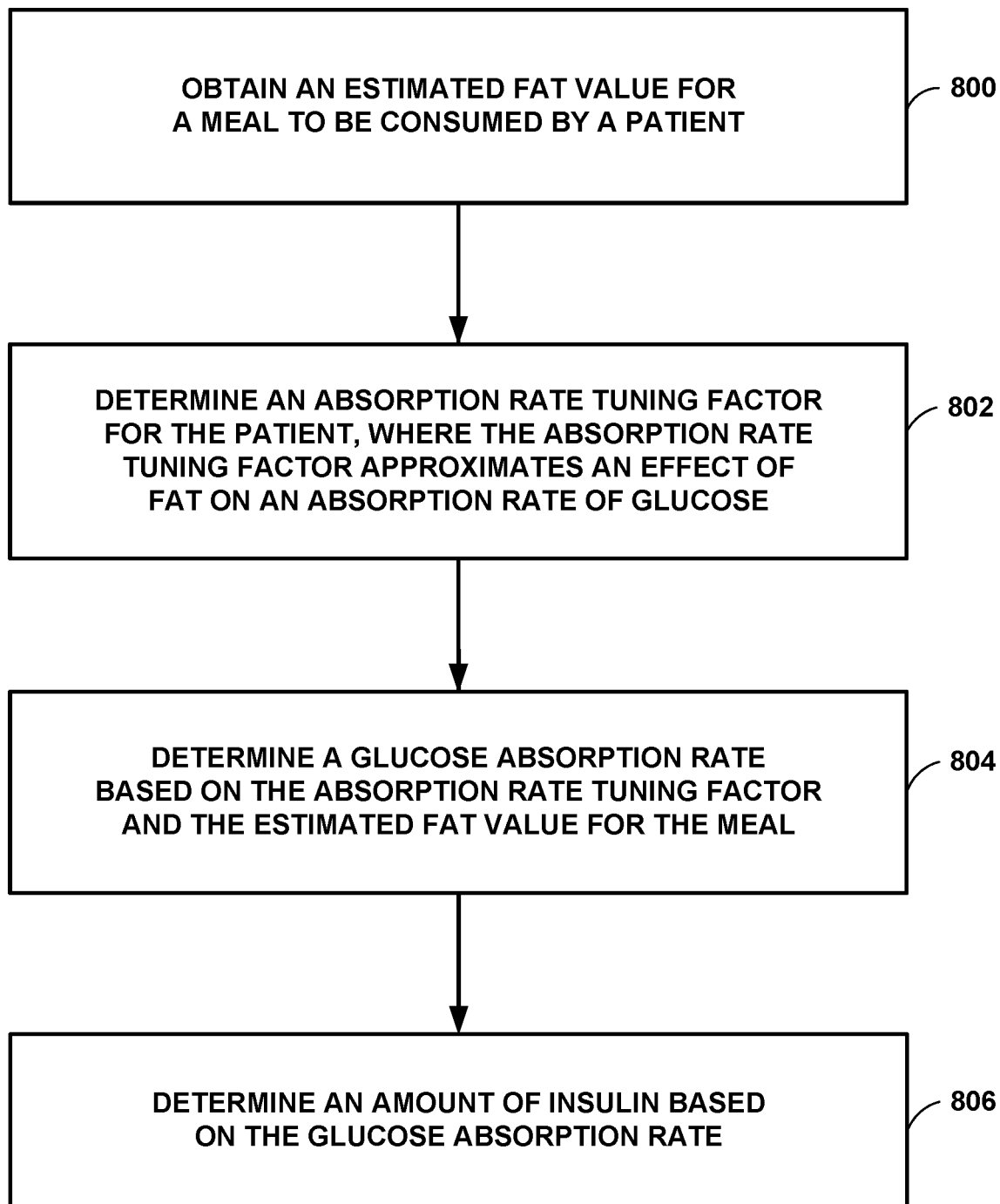

FIGS. 6-8 are flow diagrams illustrating example techniques for glucose level management, in accordance with the techniques of this disclosure. The example techniques can be performed by one or more processors such as one or more processors 28, processing circuitry 32, and/or one or more processors of insulin pump 14.

One or more processors 28 may be configured to obtain one or more macronutrient values for a meal (600). For example, the one or more macronutrient values may be obtained from patient device 24. In some embodiments, the one or more macronutrient values may include an estimated carbohydrate value for the meal. Additionally or alternatively, the one or more macronutrient values may include an estimated protein value and/or an estimated fat value for the meal. One or more processors 28 can use the one or more macronutrient values to determine the rate at which the digestive system of patient 12 absorbs glucose molecules.

One or more processors 28 may be configured to determine an amount of insulin to deliver to patient 12 to counteract a glucose level increase caused by consumption of the meal (602). The amount of insulin may correspond to a meal bolus.

In some embodiments, the amount of insulin may be determined based on using a digital twin of patient 12 to predict amounts of glucose to be absorbed into the bloodstream of patient 12 over a duration of time due to consumption of the meal. For example, as mentioned above, one or more processors 28 may determine a glucose absorption rate of the digestive system based on the one or more macronutrient values. Based on the glucose absorption rate of the digestive system, one or more processors 28 may predict amounts of glucose to be absorbed into the bloodstream of patient 12 over a duration of time due to consumption of the meal. More specifically, the predicted amounts of glucose to be absorbed into the bloodstream over time may be derived from the glucose absorption rate of the digestive system based on the speed of carbohydrate absorption for patient 12. As will be described in greater detail below, the predicted amounts of glucose to be absorbed into the bloodstream may be used to determine a bolus dosage of insulin to deliver to patient 12.

In some embodiments, the bolus dosage may be determined based on using the digital twin of patient 12 to predict postprandial glucose levels. As mentioned above, the digital twin may be configured to predict postprandial glucose levels based on the net movement of glucose into and out of the bloodstream. Glucose entering the bloodstream includes the predicted amounts of glucose to be absorbed into the bloodstream, and glucose exiting the bloodstream includes glucose absorbed into interstitial fluid due to the effects of insulin.

In some embodiments, the digital twin may predict postprandial glucose levels to determine an amount of the bolus dosage that is "optimal" in that it maximizes time-in-range. For example, one or more processors 28 may identify a plurality of candidate dosages. Based on the predicted amounts of glucose to be absorbed into the bloodstream over time and the amount of each candidate dosage, the digital twin of patient 12 may be used to predict a respective time series of glucose values for each candidate dosage. Each time series of glucose values may be evaluated to determine a respective amount of time within a target range for patient 12's glucose levels, and one or more processors 28 may select the candidate dosage that corresponds to a maximum amount of time within the target range.

In some embodiments, the digital twin may predict postprandial glucose levels to determine an amount of the bolus dosage to supplement a previously delivered amount of insulin. For example, one or more processors 28 may obtain (e.g., from patient device 24) an amount of insulin (e.g., a basal dosage) previously delivered to patient 12. Based on the amount of insulin previously delivered and the predicted amounts of glucose to be absorbed into the bloodstream, one or more processors 28 may simulate postprandial glucose levels of patient 12. Thus, one or more processors 28 may determine the bolus dosage to be an additional amount of insulin for maximizing time-in-range.

One or more processors 28 may be configured to generate an output indicative of the amount of insulin to deliver to patient 12 (604). The output may also include a time at which the insulin can be delivered to patient 12. By accounting for the estimated fat and/or protein content of a meal, one or more processors 28 may be able to generate an output that is more accurately tailored to patient 12 and to the meal to be consumed.

In some examples, one or more processors 28 are configured to cause an insulin device to deliver the determined amount of insulin as a bolus. The amount of insulin may be a single dose or multiple doses over time. Additionally or alternatively, one or more processors 28 may be configured to store the output to memory and/or transmit the output to another device. The determined amount of insulin can be automatically delivered to patient 12 and/or presented to patient 12 via a display.

In the example shown in FIG. 7, one or more processors 28 may be configured to obtain an estimated protein value for a meal (700). As mentioned above, one or more processors 28 may obtain the estimated protein value from patient device 24 in some examples.

One or more processors 28 may be further configured to convert the estimated protein value to a first equivalent carbohydrate value (702). One or more processors 28 can convert the estimated protein value to the first equivalent carbohydrate value by multiplying or dividing the estimated protein value by a conversion factor or by applying another mathematical function, such as an exponential or a logarithmic function, involving the conversion factor. The conversion factor may convert the estimated protein value to a parameter approximating the effect of protein on glucose levels of patient 12. For example, the digital twin may approximate the effect of protein as exhibiting a smaller (relative to carbohydrates) but linear contribution to glucose levels. Thus, the conversion factor may scale down the estimated protein value to a corresponding carbohydrate value that can be added to the estimated carbohydrate content of the meal.

Although FIG. 7 is discussed in terms of protein, a similar approach may be used for other macronutrients. For example, the fat content of a meal may also impact the total equivalent carbohydrates of the meal. Accordingly, one or more processors 28 may be configured to determine the total equivalent carbohydrate value for a meal based on the estimated fat value for the meal. However, each gram of fat in a meal may have a smaller effect on the total equivalent carbohydrate value for the meal than each gram of protein in the meal. Thus, one or more processors 28 may use a different (e.g., larger) conversion factor for fat than the conversion factor for protein.

The conversion factor may vary from patient to patient and/or from meal to meal. In some examples, one or more processors 28 may be configured to determine a patient-specific conversion factor based on historical meal data for patient 12 and further based on historical glucose level data for patient 12. In some examples, one or more processors 28 can use optimization procedures and/or machine learning to determine a best-fit conversion factor for each meal. In some examples, one or more processors 28 may be configured to determine a patient-specific conversion factor by determining the mean or median of the best-fit conversion factors. In some examples, one or more processors 28 may be configured to determine the conversion factor for a meal based on a time of day that patient 12 consumes the meal.

One or more processors 28 may be configured to determine a total equivalent carbohydrate value for the meal based on the first equivalent carbohydrate value(704). Thus, for a meal including thirty grams of carbohydrates and ten grams of protein, one or more processors 28 may first convert the protein value to a first equivalent carbohydrate value of, for example, two grams using a conversion factor value of five. Alternatively, for a conversion factor value of ten, one or more processors 28 can determine a first equivalent carbohydrate value of one gram. One or more processors 28 may then add the first equivalent carbohydrate value to the estimated carbohydrate value to determine a total equivalent carbohydrate value for the meal of thirty-one or thirty-two grams. For two meals that are otherwise identical, one or more processors 28 may be configured to determine a higher total equivalent carbohydrate value for a meal with a higher protein value than a meal with a lower protein value.

One or more processors 28 may be configured to determine an amount of insulin based on the total equivalent carbohydrate value (706). In some examples, based on the total equivalent carbohydrate value for the meal, the digital twin of patient 12 may be used to predict amounts of glucose to be absorbed into the bloodstream of patient 12 over a duration of time due to consumption of the meal.

In the example shown in FIG. 8, one or more processors 28 may be configured to obtain an estimated fat value for a meal (800). As mentioned above, one or more processors 28 may obtain the estimated fat value from patient device 24 in some examples.

One or more processors 28 may be further configured to determine an absorption rate tuning factor for patient 12, where the absorption rate tuning factor approximates an effect of fat on an absorption rate of glucose (802). In some embodiments, the absorption rate tuning factor may be used to approximate or limit the effect of fat on reducing the glucose absorption rate.

The absorption rate tuning factor may vary from patient to patient and/or from meal to meal. In some examples, one or more processors 28 may be configured to determine a patient-specific absorption rate tuning factor based on historical meal data for patient 12 and further based on historical glucose level data for patient 12. In some examples, one or more processors 28 can use optimization procedures and/or machine learning to determine a best-fit absorption rate tuning factor for each meal. In some examples, one or more processors 28 may be configured to determine a patient-specific absorption rate tuning factor by determining the mean or median of the best-fit absorption rate tuning factors. In some examples, one or more processors 28 may be configured to periodically update the absorption rate tuning factor, because a patient-specific absorption rate tuning factor can change over time (e.g., over months or years). In some examples, one or more processors 28 may be configured to determine the absorption rate tuning factor for a meal based on a time of day that patient 12 consumes the meal.

One or more processors 28 may be configured to determine a glucose absorption rate based on the absorption rate tuning factor and the estimated fat value for the meal (804). The glucose absorption rate may correspond to the rate at which glucose is absorbed by the digestive system into the bloodstream of patient 12. In some examples, one or more processors 28 are configured to determine that a first meal will have a faster absorption rate than a second meal if the first meal has a lower fat content, assuming that the first and second meals are otherwise identical.

One or more processors 28 may be configured to use Equation (1) shown below for determining a glucose absorption rate, which is represented by S, based on the estimated fat value and the absorption rate tuning factor, which is represented by omega. The glucose absorption rate in Equation (1) may become saturated towards an upper limit as the fat value in the meal increases. Equation (1) also includes optional variables $C_1$ and $C_2$. In some examples, one or more processors 28 may be configured to use a value of the speed of carbohydrate absorption, or a multiple thereof, as a value for the variable $C_1$. For very large fat contents or very small values of omega, the glucose absorption rate may approach (e.g., asymptotically approach) $C_2$. For very low fat contents or very large values of omega, the glucose absorption rate may approach (e.g., asymptotically approach) $C_1+C_2$.

$$S = C_1 \times \frac{\Omega}{\text{fat} + \Omega} + C_2 \qquad (1)$$

Although FIG. 8 is discussed in terms of fat, a similar approach may be used for other macronutrients. For example, one or more processors 28 may be configured to determine the glucose absorption rate based on the protein value of the meal, but the protein value may have a smaller effect on the glucose absorption rate than the fat value.

One or more processors 28 may be configured to determine an amount of insulin based on the glucose absorption rate (806). In some examples, based on the glucose absorption rate, one or more processors 28 may determine a peak of the glucose level increase caused by consumption of the meal. In some examples, based on the glucose absorption rate, one or more processors 28 may further determine a timing for the peak.

The following numbered examples demonstrate one or more aspects of the disclosure.

Example 1. A processor-implemented method includes obtaining an estimated protein value for a meal and determining an equivalent carbohydrate value for the meal based on the estimated protein value. The method also includes determining, based on the equivalent carbohydrate value for the meal, an amount of insulin to deliver to a patient to counteract a glucose level increase caused by consumption of the meal. The method further includes generating an output indicative of the amount of insulin to deliver to the patient to counteract the glucose level increase caused by consumption of the meal.

Example 2. The method of example 1, further including obtaining an estimated fat value for a meal, determining, based on the estimated fat value, a glucose absorption rate resulting from consumption of the meal, wherein determining the amount of insulin to deliver to the patient is based on the equivalent carbohydrate value for the meal and is further based on the glucose absorption rate resulting from consumption of the meal.

Example 3. A method includes obtaining an estimated fat value for a meal and determining, based on the estimated fat value, a glucose absorption rate resulting from consumption of the meal. The method also includes determining, based on the glucose absorption rate resulting from consumption of the meal, an amount of insulin to deliver to a patient to counteract a glucose level increase caused by consumption of the meal. The method further includes generating an output indicative of the amount of insulin to deliver to the patient to counteract the glucose level increase caused by consumption of the meal.

Example 4. The method of example 3, further including obtaining an estimated protein value for a meal, determining an equivalent carbohydrate value for the meal based on the estimated protein value meal, wherein determining the amount of insulin to deliver to the patient is based on the glucose absorption rate resulting from consumption of the meal and is further based on the equivalent carbohydrate value for the meal.

Example 5. The method of the preceding examples or any combination thereof, wherein determining the amount of insulin to deliver to the patient includes predicting, based on the equivalent carbohydrate value for the meal, amounts of glucose to be absorbed into a bloodstream of the patient over a duration of time due to consumption of the meal.

Example 6. The method of the preceding examples or any combination thereof, wherein determining the amount of insulin to deliver to the patient includes determining, based on the predicted amounts of glucose to be absorbed into the bloodstream, a bolus dosage of insulin to deliver to the patient.

Example 7. The method of example 4, wherein determining the amount of insulin to deliver to the patient includes prior to determining the bolus dosage, obtaining an amount of a basal dosage of insulin previously delivered to the patient, and wherein determining the bolus dosage is further based on the amount of the basal dosage of insulin.

Example 8. The method of the preceding examples or any combination thereof, wherein determining a bolus dosage includes identifying a plurality of candidate dosages and, for each candidate dosage of the plurality of candidate dosages, predicting a respective amount of time within a target range for the patient's glucose levels, Example 9. The method of the preceding examples or any combination thereof, wherein determining a bolus dosage includes selecting a candidate dosage that results in a maximum amount of time within the target range.

Example 10. The method of the preceding examples or any combination thereof, wherein determining the equivalent carbohydrate value includes determining a conversion factor for converting protein to a parameter approximating an effect of the protein on glucose levels of the patient.

Example 11. The method of the preceding examples or any combination thereof, wherein determining the equivalent carbohydrate value includes determining the equivalent carbohydrate for the meal based on the estimated protein value for the meal and the conversion factor.

Example 12. The method of the preceding examples or any combination thereof, wherein the conversion factor is determined based on historical meal data for the patient and further based on historical glucose level data for the patient.

Example 13. The method of the preceding examples or any combination thereof, wherein the conversion factor is determined based on a time of day that the patient consumes the meal.

Example 14. The method of the preceding examples or any combination thereof, wherein determining the glucose absorption rate includes determining an absorption rate tuning factor for approximating an effect of fat on the glucose absorption rate.

Example 15. The method of the preceding examples or any combination thereof, wherein determining the glucose absorption rate includes determining the glucose absorption rate based on the estimated fat value for the meal and the absorption rate tuning factor.

Example 16. The method of the preceding examples or any combination thereof, wherein an absorption rate tuning factor is determined based on historical meal data for the patient and further based on historical glucose level data for the patient.

Example 17. The method of the preceding examples or any combination thereof, wherein determining the amount of insulin to deliver to the patient includes determining, based on the glucose absorption rate, a peak of the glucose level increase caused by consumption of the meal.

Example 18. The method of the preceding examples or any combination thereof, wherein determining the amount of insulin to deliver to the patient includes determining, based on the peak, the amount of insulin to deliver to the patient.

Example 19. The method of the preceding examples or any combination thereof, wherein determining the amount of insulin to deliver to the patient includes determining, based on the glucose absorption rate, a timing for a peak of the glucose level increase cause by consumption of the meal.

Example 20. The method of the preceding examples or any combination thereof, wherein determining the amount of insulin to deliver to the patient includes determining, based on the timing for the peak, the amount of insulin to deliver to the patient.

Example 21. A system includes one or more processors and one or more processor-readable storage media storing instructions which, when executed by the one or more processors, cause performance of the method of the preceding examples or any combination thereof.

Example 22. A device includes a computer-readable medium having executable instructions stored thereon, configured to be executable by processing circuitry for causing the processing circuitry to perform the method of the preceding examples or any combination thereof.

Example 23. A system comprising means for performing the method of the preceding examples or any combination thereof.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:
1. A system comprising:
an insulin infusion device;
one or more processors; and
one or more processor-readable storage media storing instructions which, when executed by the one or more processors, cause performance of:
obtaining an estimated fat value for a meal;
determining, based on the estimated fat value, a glucose absorption rate resulting from consumption of the meal by using a patient-specific parameter to determine the glucose absorption rate that is scaled between two values;
predicting, using a patient-specific physiological simulator and based on the glucose absorption rate, amounts of glucose to be absorbed in a bloodstream of the patient and a glucose level increase over a period of time that is caused by the consumption of the meal;
determining, based on the predicted amounts of glucose to be absorbed in the bloodstream of the patient and the predicted glucose level increase over the period of time, an amount of insulin to deliver to a patient that counteracts the predicted glucose level increase over the period of time that is caused by consumption of the meal;

generating an output indicative of the amount of insulin to deliver to the patient to counteract the glucose level increase caused by consumption of the meal; and delivering, by the insulin infusion device, the determined amount of insulin to the patient based on the output.

2. The system of claim 1, wherein determining the amount of insulin to deliver to the patient comprises:

determining, based on the predicted amounts of glucose to be absorbed into the bloodstream, a bolus dosage of insulin to deliver to the patient.

3. The system of claim 2, wherein determining the amount of insulin to deliver to the patient comprises:

prior to determining the bolus dosage, obtaining an amount of a basal dosage of insulin previously delivered to the patient, and wherein determining the bolus dosage is further based on the amount of the basal dosage of insulin.

4. The system of claim 2, wherein determining the bolus dosage comprises:

identifying a plurality of candidate dosages;

for each candidate dosage of the plurality of candidate dosages, predicting a respective amount of time within a target range for the patient's glucose levels; and selecting a candidate dosage that corresponds to a maximum amount of time within the target range.

5. The system of claim 1, wherein determining the glucose absorption rate comprises:

determining an absorption rate tuning factor for approximating an effect of fat on the glucose absorption rate, wherein the absorption rate tuning factor is the patient-specific parameter; and determining the glucose absorption rate based on the estimated fat value for the meal and the absorption rate tuning factor.

6. The system of claim 5, wherein the absorption rate tuning factor is determined based on historical meal data for the patient and further based on historical glucose level data for the patient.

7. The system of claim 1, wherein determining the amount of insulin to deliver to the patient comprises:

determining, based on the glucose absorption rate, a peak of the glucose level increase caused by consumption of the meal; and determining, based on the peak, the amount of insulin to deliver to the patient.

8. The system of claim 1, wherein determining the amount of insulin to deliver to the patient comprises:

determining, based on the glucose absorption rate, a timing for a peak of the glucose level increase caused by consumption of the meal; and determining, based on the timing for the peak, the amount of insulin to deliver to the patient.

9. A processor-implemented method comprising:

obtaining an estimated fat value for a meal;

determining, based on the estimated fat value, a glucose absorption rate resulting from consumption of the meal by using a patient-specific parameter to determine the glucose absorption rate that is scaled between two values;

predicting, using a patient-specific physiological simulator and based on the glucose absorption rate, amounts of glucose to be absorbed in a bloodstream of the patient and a glucose level increase over a period of time that is caused by the consumption of the meal;

determining, based on the predicted amounts of glucose to be absorbed in the bloodstream of the patient and the predicted glucose level increase over the period of time, an amount of insulin to deliver to a patient that counteracts the predicted glucose level increase over the period of time that is caused by consumption of the meal;

generating an output indicative of the amount of insulin to deliver to the patient to counteract the glucose level increase caused by consumption of the meal; and delivering, by an insulin infusion device, the determined amount of insulin to the patient based on the output.

10. The method of claim 9, wherein determining the amount of insulin to deliver to the patient comprises:

determining, based on the predicted amounts of glucose to be absorbed into the bloodstream, a bolus dosage of insulin to deliver to the patient.

11. The method of claim 10, wherein determining the amount of insulin to deliver to the patient comprises:

prior to determining the bolus dosage, obtaining an amount of a basal dosage of insulin previously delivered to the patient, and wherein determining the bolus dosage is further based on the amount of the basal dosage of insulin.

12. The method of claim 10, wherein determining the bolus dosage comprises:

identifying a plurality of candidate dosages;

for each candidate dosage of the plurality of candidate dosages, predicting a respective amount of time within a target range for the patient's glucose levels; and selecting a candidate dosage that corresponds to a maximum amount of time within the target range.

13. The method of claim 9, wherein determining the glucose absorption rate comprises:

determining an absorption rate tuning factor for approximating an effect of fat on the glucose absorption rate, wherein the absorption rate tuning factor is the patient-specific parameter; and determining the glucose absorption rate based on the estimated fat value for the meal and the absorption rate tuning factor.

14. The method of claim 13, wherein the absorption rate tuning factor is determined based on historical meal data for the patient and further based on historical glucose level data for the patient.

15. The method of claim 9, wherein determining the amount of insulin to deliver to the patient comprises:

determining, based on the glucose absorption rate, a peak of the glucose level increase caused by consumption of the meal; and determining, based on the peak, the amount of insulin to deliver to the patient.

16. The method of claim 9, wherein determining the amount of insulin to deliver to the patient comprises:

determining, based on the glucose absorption rate, a timing for a peak of the glucose level increase caused by consumption of the meal; and determining, based on the timing for the peak, the amount of insulin to deliver to the patient.

17. One or more non-transitory processor-readable storage media storing instructions which, when executed by one or more processors, cause performance of:

obtaining an estimated fat value for a meal;

determining, based on the estimated fat value, a glucose absorption rate resulting from consumption of the meal by using a patient-specific parameter to determine the glucose absorption rate that is scaled between two values;

predicting, using a patient-specific physiological simulator and based on the glucose absorption rate, amounts of glucose to be absorbed in a bloodstream of the patient and a glucose level increase over a period of time that is caused by the consumption of the meal;

determining, based on the predicted amounts of glucose to be absorbed in the bloodstream of the patient and the predicted glucose level increase over the period of time, an amount of insulin to deliver to a patient that counteracts the predicted glucose level increase over the period of time that is caused by consumption of the meal;

generating an output indicative of the amount of insulin to deliver to the patient to counteract the glucose level increase caused by consumption of the meal; and delivering, by an insulin infusion device, the determined amount of insulin to the patient based on the output.

18. The one or more non-transitory processor-readable storage media of claim 17, wherein determining the glucose absorption rate comprises:

determining an absorption rate tuning factor for approximating an effect of fat on the glucose absorption rate, wherein the absorption rate tuning factor is the patient-specific parameter; and determining the glucose absorption rate based on the estimated fat value for the meal and the absorption rate tuning factor.

19. The one or more non-transitory processor-readable storage media of claim 18, wherein the absorption rate tuning factor is determined based on historical meal data for the patient and further based on historical glucose level data for the patient.

20. The one or more non-transitory processor-readable storage media of claim 17, wherein determining the amount of insulin to deliver to the patient comprises:

determining, based on the glucose absorption rate, a timing for a peak of the glucose level increase caused by consumption of the meal; and determining, based on the timing for the peak, the amount of insulin to deliver to the patient.

* * * * *